US00RE35462E

United States Patent [19]

Haas et al.

[11] E Patent Number: Re. 35,462

[45] Reissued Date of Patent: Feb. 25, 1997

[54] SILYLATED BENZOIC ACID DERIVATIVES

[75] Inventors: Wolfgang Haas, Germering; Norman Häberle; Rainer Winkler, both of Munich; Franz-Heinrich Kreuzer, Martinsried, all of Germany

[73] Assignee: Consortium fur elekochemische Ind. GmbH, Munich, Germany

[21] Appl. No.: 192,515

[22] Filed: Feb. 7, 1994

Related U.S. Patent Documents

Reissue of:

[64] Patent No.: 5,106,530
Issued: Apr. 21, 1992
Appl. No.: 542,477
Filed: Jun. 22, 1990

[30] Foreign Application Priority Data

Jun. 22, 1989 [DE] Germany ..... 3920509
Apr. 24, 1990 [DE] Germany ..... 4013067

[51] Int. Cl.[6] ..... C09K 19/06; C09K 19/34; C07F 7/04; C07F 7/08

[52] U.S. Cl. ..... 252/299.6; 252/299.61; 252/299.63; 252/299.64; 252/299.65; 252/299.66; 252/299.67; 556/413; 556/417; 556/418; 556/434; 556/437; 556/438; 556/439; 556/453; 556/454; 556/456; 556/457

[58] Field of Search ..... 252/299.6, 299.61, 252/299.62, 299.64, 299.65, 299.66, 299.67; 556/413, 417, 418, 434, 437, 438, 439, 453, 454, 456, 457

[56] References Cited

U.S. PATENT DOCUMENTS

| | | | |
|---|---|---|---|
| 4,358,391 | 11/1982 | Finkelmann et al. | 252/299.01 |
| 4,769,448 | 9/1988 | Heeger et al. | 534/804 |
| 4,774,028 | 9/1988 | Imai et al. | 252/299.01 |
| 4,835,235 | 5/1989 | DeMartino et al. | 526/311 |
| 5,188,762 | 2/1993 | Iwaki et al. | 252/299.62 |

FOREIGN PATENT DOCUMENTS

| | | |
|---|---|---|
| 0141512 | 5/1985 | European Pat. Off. . |
| 0162395 | 12/1985 | European Pat. Off. . |
| 0304720 | 3/1989 | European Pat. Off. . |
| 0322703 | 7/1989 | European Pat. Off. . |
| 0333022 | 9/1989 | European Pat. Off. . |
| 0338576 | 10/1989 | European Pat. Off. . |
| 0354753 | 2/1990 | European Pat. Off. . |
| 0358208 | 3/1990 | European Pat. Off. . |
| 3827600 | 2/1990 | Germany . |
| 1-144491 | 6/1989 | Japan . |

OTHER PUBLICATIONS

Molecular Crystals & Liquid Crystals, Band 157, Apr. 1988, Seiten 57–67, Montreaux, CH; B. W. Jo et al.

Polymer Bulletin, Band 12, No. 5, Nov. 1984, Seiten 383–388, Springer–Verlag, Heidelberg, DE; C. Aquilera et al.

Chemical Abstracts, Band 109, 1988, Seite 622, Zusammenfassung No. 37871e, Columbus, Ohio, US; B. L. Rivas et al.

Chemical Abstracts, vol. 111, 1989, p. 742, No. 205667e.

Haruhara Kazuyuki et al., "Ferroelectric Chirol Smectic Liquid Crystal Materials".

Young, W. R. et al., Mol. Cryst. Liq. Cryst., vol. 13, pp. 305–321. (1971).

*Primary Examiner*—Shean Wu
*Attorney, Agent, or Firm*—Martin Connaughton

[57] ABSTRACT

The present invention relates to compounds of the formula

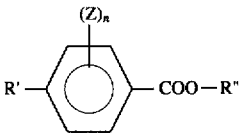

(8)

in which

Z is a halogen atom, a cyano group or a hydroxyl group, n is 0, 1 or 2,

R' is a radical of the formula $$R'''—[Si(R^*)_2]_x(CH_2)_yR''''— \quad (9),$$

in which x is the number 0 or 1, y is an integer from 1 to 18,

R'''is a defined in the description,

R* is identical or different, optionally substituted $C_1$- to $C_{18}$-hydrocarbon or hydrocarbonoxy radicals, R'''' is a phenylene or biphenylene radical or a radical of the formula —E—, where E is a divalent radical of the formula —O— or $—[Si(R^*)_2]_z—$, and z is the number 0 or 1, and the compounds contain at least one group of the formula $—Si(R^*)_2—$ per molecule, and the radical R" is a cholesteryl radical, a radical as defined for R* or a radical of the formula $—C_6H_4—R^*$, and the preparation and use thereof.

2 Claims, No Drawings

SILYLATED BENZOIC ACID DERIVATIVES

Matter enclosed in heavy brackets [ ] appears in the original patent but forms no part of this reissue specification; matter printed in italics indicates the additions made by reissue.

The invention relates to novel silylated benzoic acid derivatives, some of which are liquid-crystalline, a process for their preparation, and their use.

PRIOR ART

Liquid-crystalline compounds are described, inter alia, by D. Demus, H. Demus and H. Zaschke (Flüssige Kristalle in Tabellen [Liquid Crystals in Tables], 1974; D. Demus and H. Zaschke. Flüssige Kristalle in Tabellen II [Liquid Crystals in Tables II], 1984, VEB-Verlag Leipzig). U.S. Pat. No. 4,358, 391 (H. Finkelmann et at., Wacker-Chemie GmbH) describes liquid-crystalline polymers having an organopolysiloxane backbone and mesogenic side groups. M. Petrzilka et at. (EP-A-122,389, F. Hoffmann-La Roche & Co.) claim liquid crystal components having an alkenyl chain, it also being possible for a benzoic acid derivative to be attached to this alkenyl chain. These compounds do not contain organosilicon groups. W. R. Young et al. (Molecular Crystals and Liquid Crystals, Vol. 13, pages 305–321, 1971, Gordon and Breach Science Publishers) report, inter alia, 4'-silylated benzimides of 4-aminophenol benzoates. At the bottom of page 309, they mention that these silicon-containing esters, in contrast to comparable substances, do not form a mesomorphic phase, which is attributed to the steric hinderance of the organosilyl group.

OBJECT

The object of the present invention was to synthesize novel, preferably liquid-crystalline compounds, in particular those containing organosilicon groups. It was a further object of the present invention to prepare liquid-crystalline compounds which are readily miscible with other liquid crystals, and are colorless and of low viscosity. It was also an object of the present invention to prepare liquid-crystalline compounds which are highly suitable as dielectrics in display devices and in particular by means of which short addressing times and high contrasts can be achieved in such devices.

DESCRIPTION

The abovementioned objects are achieved by the present invention through compounds of the formula

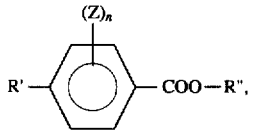

(8)

in which

Z is a halogen atom, a cyano group or a hydroxyl group, n is 0, 1 or 2,

R' is a radical of the formula $$R'''—[Si(R^*)_2]_x(CH_2)_yR''''— \quad (9),$$

in which x is the number 0 or 1, y is an integer from 1 to 18,

R''' is a $C_1$— to $C_8$-alkyl radical, a radical of the formula $R^*—[Si(R^*)_2O]_v—$, where v is an integer having a value of from 1 to 10, or a radical of the formula

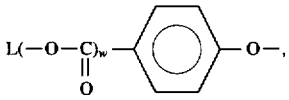

(3)

in which w is the number 0 or 1, and

L is a cholesteryl radial or a phenyl radical which is optionally substituted by phenyl, halogen, cyano and/or $C_1$— to $C_4$— alkoxy radicals, or, if w=0, may alternatively be a halogen atom, a cyano radical or a $C_1$–$C_4$-alkoxy radical;

R* is identical or different, straight-chain or branched, optionally substituted $C_1$- to $C_{18}$- hydrocarbon or hydrocarbonoxy radicals, R'''' is a phenylene or biphenylene radical or radical of the formula —E—, where E is a divalent radical of the formula —O— or $—[Si(R^*)_2]_z—$, and z is the number 0 or 1, and the sum of the indices x+v+z must be at least one, so that the compounds contain at least one group of the formula $—Si(R^*)_2$13 per molecule, and the radical R" is a cholesteryl radical, a radical as defined for R* or a radical of the formula $—C_6H_4—R^*$.

n preferably has the value 0 or 1, in particular 0.

Preferred substituents for the radicals R* are fluorine or chlorine atoms, cyano radicals and oxiranyl radicals. If the radical R* is a branched radical, it is preferred that the radical R* is branched along its longest chain by methyl groups.

R''' may preferably only be a radical of the formula (3) if x has the value 0.

The chains formed by the compounds of the formula (8) may be extended by further structural units selected from the group comprising the radicals B, namely the phenylene, cyclohexylene, pyridinediyl, pyrimidinediyl, pyridazinediyl, triazinediyl, tetrzinediyl, dioxanediyl, tetrahydrofurandiy. bicyclo[2.2.2]octanediyl and cholesteryl radicals, and the radicals D, namely the carbonyloxy, oxycarbonyl, $—CH_{-2}—CH_2—$, $—O—CH_2—$ and $—CH_2—O—$ groups and radicals of the formulae —CH=CH—, —N=CH—, —CH=N—, —C=C—, —N=N—, —N=N(O)— and —O—, with the proviso that the abovementioned radical and groups, if possible, may be substituted by $C_1$- to $C_{18}$-alkyl radicals, phenyl radicals or polar radicals, preferably halogen atoms, cyano groups of hydroxyl groups, and none of the radicals D are linked directly to one another.

The further structural units which extend the chain are preferably selected from the group comprising the 1,4-phenylene, 1,4-cyclohexylene, 2,5-pyridinediyl, 2,5-pyrimidinediyl,3,6-pyridazinediyl,3,6-triazinediyl, 3,6-tetrazinediyl, 2,5-dioxanediyl, 2,5-tetrahydrofurandiyl, bicyclo [2.2.2]octanediyl and cholesteryl radicals and carbonyloxy, oxycarbonyl, $—CH_2—CH_2—$, $—O—CH_2—$ and $—CH_2—O—$ groups, radicals of the formulae —CH=CH—, —N=CH—, —CH=N—, —C=C—, —N=N—, —N=N(O)— and —O—, with the proviso that the abovementioned radicals and groups, if possible, may be substituted by $C_1$- to $C_{18}$-alkyl radicals, phenyl radicals or polar radicals, preferably halogen atoms, cyano groups or hydroxyl groups.

The compounds of the formula (8) are preferably those of the formula (30):

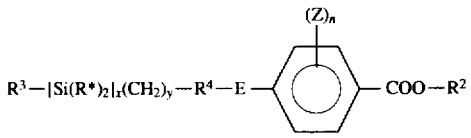

(30)

where Z and n are as defined in claim 1, and in which $R^3$ is a $C_1$- to $C_8$-alkyl radical, a radical of the formula $R^1$—$R^4$—$[Si(R^*)_2O]_v$—, where $R^1$ is a halogen atom, a cyano radical, a cholesteryl radical, a hydrogen atom, a hydroxyl radical or a radical as defined for R* or —O—R*, and v is an integer having a value of from [0] *1* to 10, R* is identical or different, optionally substituted $C_1$- to $C_{18}$-hydrocarbon radicals, x is the number 0 or 1, y is an integer from 1 to 18, E is a divalent radical of the formula —O— or —$[-Si(R^*)_2]_z$—, and z is the number 0 or 1, and the sum of the indices x+v+z, except in the radical $R^2$, must be at least one, and the radical $R^4$ is identical or different radicals of the formula —$[(B)_b(D)_d]_c$—, where each of the radicals B and D may be as defined above and in claim 2, with the proviso that none of the radicals D are linked directly to one another, and each of the indices b and c are identical or different integers having a value of from 0 to 6, and d is in each case the number 0 or 1, $R^2$ is a monovalent radical of the formula —$R^4$—$R^1$ or —$R^4$—$(CH_2)_y[Si(R^*)_2]_x$—$R^3$.

The condition that the sum x+v+z, except in the radical $R^2$, must be at least one should be interpreted as meaning that the condition mentioned must apply to the moiety of the formula (30) indicated by the formula

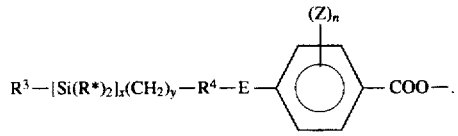

The compounds according to the invention preferably contain a maximum of seven radicals as defined for B, including the phenylene radicals reproduced in the formulae (8), (3) and (30).

Preferred compounds according to the invention are those compounds of the formula (30) in which $R^1$is a halogen atom, preferably a chlorine atom, a cyano group, a hydrogen atom, a hydroxyl group, a $C_1$–to $C_{18}$-alkoxy group, preferably a $C_1$- to $C_8$-alkoxy group, a $C_1$- to $C_{18}$-alkyl group, preferably a $C_1$- to $C_8$-alkyl group, or a cholesteryl radical, and/or $R^3$ is a radical of the formula $R^1$—$R^4$—$[Si(CH_3)_2O]_v$—, and/or $R^4$ is a single chemical bond, a —$CH_2$—$CH_2$— radical, a radical of the formula —O—, a radical selected from the group comprising the optionally halogenated, divalent radicals of the formulae

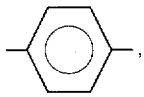

(42)

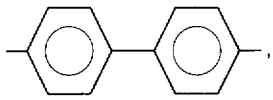

(43)

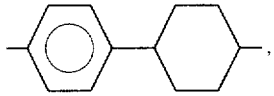

(44)

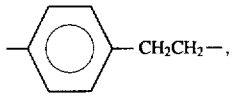

(45)

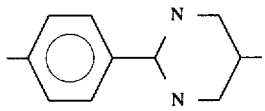

(46)

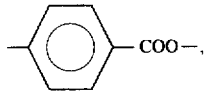

(47)

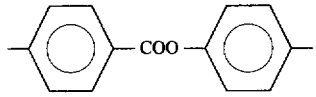

(48)

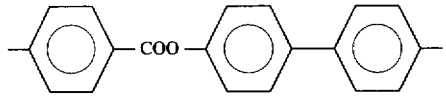

(49)

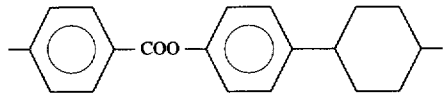

(50)

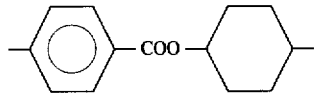

(51)

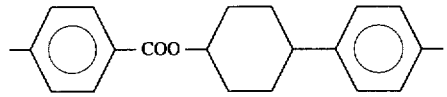

(52)

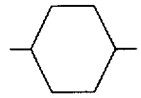

(59)

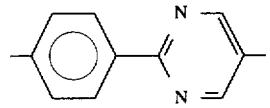

(60)

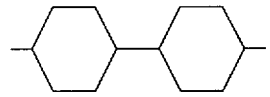

(61)

v is the number [0,] 1 or 2 and/or x is the number 1, and/or y is an integer from 3 to 12, and/or $R^2$ is a radical of the formula $—R^4—R^1$ or $—R^4—(CH_2)_y—Si(CH_3)_2—[OSi(CH_3)_2]_vR^4—R^1$ and the respective other radicals are as defined under formula (30) and, as for the formula (30), the sum of the indices x+v+z, except in the radical $R^2$, must be at least one.

For the compounds of the formula (30), preferably at least two, particularly preferably at least three, in particular at least four, specifically at least five, particularly specifically at least six, very specifically all seven of the abovementioned conditions are fulfilled.

Of the abovementioned compounds, the liquid-crystalline compounds are preferred.

Preparation processes Process 1

Compounds of the formula (8) or of the formula (30) can be prepared by reacting compounds of the formula

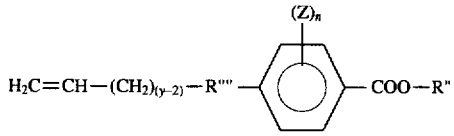

(10)

with compounds of the formula $$R'''—[Si(R^*)_2]_x—H \quad (12)$$

or by reacting compounds of the formula

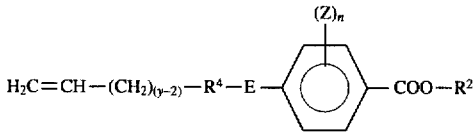

(31)

with compounds of the formula $$R^3—[Si(R^*)_2]_x—H \quad 32)$$

in the presence of platinum metals and/or compounds thereof, where, in the above formulae (10), (12), (31) and (32), x, y, E, R", R''', R'''' and R* are as defined in the formula (8) and $R^2$, $R^3$ and $R^4$ are as defined in the formula (30).

The platinum metals and/or compounds thereof employed are preferably platinum and/or compounds thereof. All catalysts which have also been employed hitherto for the addition reaction of hydrogen atoms bonded directly to Si atoms with aliphatically unsaturated compounds can be employed here. Examples of such catalysts are metallic and freely divided platinum, which may be on supports, such as silicon dioxide, aluminum oxide or activated charcoal, compounds or complexes of platinum, such as platinum halides, for example $PtCl_4$, $H_2PtCl_6.6H_2O$, $Na_2PtCl_4.H_2O$, platinum-olefin complexes, platinum-alcohol complexes, platinum-alcoholate complexes, platinum-ether complexes, platinum-ether complexes, platinum-ketone complexes, including products of reaction of $H_2PtCl_6.6H_2O$ and cyclohexanone, platinum-vinylsiloxane complexes, in particular platinum-divinyltetramethyldisiloxane complexes containing or not containing detectable inorganically bound halogen, bis-(gamma-picoline)platinum dichloride, trimethylenedipyridineplatinum dichloride, dicyclopentadieneplatinum dichlonde, (dimethyl sulfoxide)ethyleneplatinum(II) dichloride and products of the reaction of platinum tetrachloride with olefins and primary amines or secondary amines or primary and secondary amines, such as the product of the reaction of platinum tetrachloride dissolved in 1-octene with sec.- butylamine, or ammonium-platinum complexes as in EP-B 110,370.

The platinum catalyst is preferably employed in amounts of from 0.1 to 50 mol%, based on the number of moles of those starting materials of the formulae (10) or (12), or (31) or (32) which are present in the stoichiometric a mount or less.

The reaction is preferably carried out at temperatures of from 0° C. to 110° C., preferably at pressures of from 0.05 MPa to 1.0 MPa.

If the compounds of the formulae (10) and (12) or (31) and (32) should be very inert, the reaction can also be carried out at elevated temperatures, elevated pressures and in the presence of more platinum catalyst.

The reaction is preferably carried out in a solvent, which should in particular be aprotic; solvents or solvent mixtures having a boiling point or boiling range of up to 160° C., in particular of up to 120° C., in each case at 0.1 MPa (abs.), are preferred. Examples of solvents are esters, such as methyl acetate, ethyl acetate, n- and iso-propylacetate, n-, sec.- and t.-butyl acetate, ethyl formate and diethyl carbonate; ethers such as dioxane, tetrahydrofuran, diethyl ether, di-n-propyl ether, diisopropyl ether, di-n-butyl ether, ethylene glycol monomethyl ether, ethylene glycol monoethyl ether, diethylene glycol dimethyl ether and anisole; chlorinated hydrocarbons, such as dichloromethane, trichloromethane, tetrachloromethane, 1,2-dichloroethane, trichloroethylene, tetrachloroethylene and chlorobenzene; hydrocarbons, such as pentane, n-hexane, hexane isomer mixtures, cyclohexane, heptane, octane, ligroin, petroleum ether, benzene, toluene and xylenes; ketones, such as acetone, methyl ethyl ketone and methyl isobutyl ketone; carbon disulfide, pyridine, acetonitrile and nitrobenzene, or mixtures of these solvents.

The term solvent does not mean that all the reaction components must be soluble therein. The reaction can also be carried out in a suspension or emulsion of one or more reactants. The reaction can also be carried out in a solvent mixture with a miscibility gap, in which case at least one reactant is soluble in each of the mixing phases.

The compounds (10) or (31) and the compound of the formula (12) or (32) are preferably employed in the process according to the invention in the molar ratio 1:2 to 2:1, in particular 1:1.1 to 1.1:1.

Some of the compounds of the formulae (10), (12), (31) and (32) are commercial products. They can be prepared from known compounds using known methods (for example as described in: Houben-Weyl-Müller, Methoden der Organischen Chemie [Methods of Organic Chemistry], Georg Thieme Verlag, Stuttgart).

Novel intermediates

However, the compounds of the abovementioned formula (32)

$$R^3—[Si(R^*)_2]_x—H \quad (32)$$

in which x has the value 1, $R^3$ is a radical of the formula $R^1$–$R^4$-, and $R^4$ is selected from the radicals of the abovementioned formulae (47), (48), (49), (50), (51) and (52), the benzene ring being bonded directly to a silicon atom, and $R^1$, R* and x being as defined under the formula (30), are novel. They can be prepared by esterfication of the corresponding acid halides.

Examples of such acid chlorides which can be used for this purpose are dimethylsilylbenzoyl chlorides. These can be obtained in accordance with U.S. patent application Ser. No. 229,188 (filed on Aug. 8, 1988, corresponds to EP-A-304,720, F. H. Kreuzer et al., Consortium für elektrochemische Industrie GmbH) from 1,4-dihalobenzene, reacting the appropriate mono Grignard compound with dimethylchlorosilane, carrying out a further reaction with magnesium, and reacting with $CO_2$, and finally reacting the 4-dimethylsilylbenzoic acid thus obtained with, for example, thionyl chloride.

Preferred novel compounds of the formula (32) are those of the formula (53):

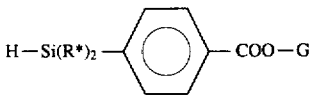

(53)

in particular those of the formula (22)

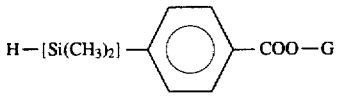

(22)

where, in the above formulae,

R* is as defined in the formula (9), and

G is a monovalent radical which is optionally bonded to the silicon atom via a divalent radical, namely a phenylene, biphenylene, cyclohexylene, phenylenecyclohexylene or cyclohexylenephenylene radical, namely a hydrogen or halogen atom or a cyano, hydroxyl, cholesteryl, $C_1$- to $C_{12}$-hydrocarbon or hydrocarbonoxy radical.

The radical G is preferably a 4-methoxyphenyl, 4-cyanophenyl, 4-chlorophenyl, trans-4-ethylcyclohexyl, (S)-2-methylbutyloxyphenol, 4-biphenylyl, 4,4'-methoxybiphenylyl, 4,4'-cyanobiphenylyl, 4-hydroxyphenyl, 4,4'-hydroxybiphenylyl, trans-4-hydroxycyclohexyl, cholesteryl or 4-cyclohexyl radical.

The novel compounds of the abovementioned formula (32)

$$R^3—[Si(R^*)_2]_x—H \quad (32)$$

in which x has the value 1, and $R^3$ is a radical of the formula $R^1—R^4—$, and $R^4$ is selected from the radicals of the abovementioned formulae (47), (48), (49), (50), (51), (52) and (59), the benzene ring being bonded directly to a silicon atom, and $R^1$, R* and x being as defined under the formula (30), i.e. preferably compounds of the formula (53), are preferably prepared by esterification of compounds of the formula (54)

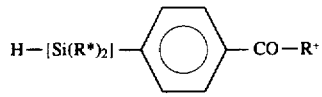

(54)

in which $R^+$ is a halogen atom or an acyl radical of a $C_2$- to $C_4$-carboxylic acid, using appropriate alcohols, i.e. in particular those of the formula G—OH.

The novel compounds can also be employed for surface-modification of supports, such as glass, quartz, silica gel etc., for example on support materials for stationary chromatographic phases. This surface modification can also be carried out, inter alia, by dotting-on or dropping-on the corresponding toluene solutions, which optionally contain platinum metals and/or compounds thereof as hydrosilylation catalyst.

Process 2

Compounds of the formula (8) and of the formula (30) can be prepared by reacting compounds of the formula

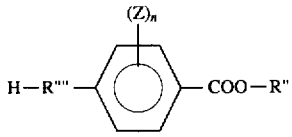

(33)

with compounds of the formula $$R'''—[Si(R^*)_2]_x(CH_2)_{(y-2)}—CH=CH_2 \quad (14)$$

or by reacting compounds of the formula

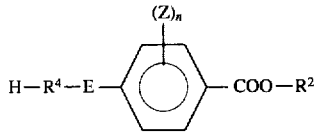

(34)

with compounds of the formula $$R^3—[Si(R^*)_2]_x(CH_2)_{(y-2)}—CH=CH_2 \quad (35)$$

in the presence of platinum metals and/or compounds therof, where, in the above formulae (14), (33), (34) and (35), E, R", R''', R'''', R*, x and y are as defined in the formula (8) and $R^2$, $R^3$ and $R^4$ are as defined in the formula (30).

Inter alia, compounds of the formula

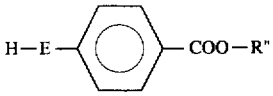

(13)

can in this way be reacted with compounds of the formula $$R'''—[Si(R^*)_2]_x(CH_2)_{(y-2)}—CH=CH_2 \quad (14)$$

in the presence of platinum metals and/or compounds thereof, where, in the above formulae (13) and (14), E, R", R''', R*, x and y are as defined m the formula (8).

Compounds of the formula (8) in which E is $—Si(CH_3)_2—$ are preferably prepared in this manner, i,e. by reacting compounds of the formula

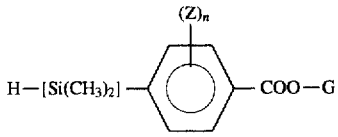

(22)

with compounds of the formula $$A—[Si(CH_3)_2]_xCH_2)_{(y-2)}—CH=CH_2 \quad (23)$$

in the presence of platinum metals and/or compounds thereof, where, in the above formulae (22) and (23), A is a $C_1$- to $C_4$-alkyl radical or a radical of the formula $$CH_3—[Si(CH_3)_2O]_2—,$$

where v is the number 1, 2 or 3,

G is as defined under the formulae (53) and (22) in process 1 described above, and x and y are as defined in the formula (9), namely x is the number 0 or 1, and y is an integer from 1 to 18.

Platinum metals and/or compounds thereof which can be employed are the corresponding metals and compounds mentioned under process 1.

The preferred reaction conditions, such as the amount ratios, pressures, temperatures and solvents, likewise correspond to those of process 1.

Correspondingly, that stated above for process 1 regarding the starting compounds (10), (12), (31) and (32) applies to the accessibility of the starting compounds (13), (14), (22), (23), (34) and (35).

Example 5 was carried out in accordance with process 2.

Process 3

The compounds of the formula (8) and of the formula (30) can also be prepared by (a) reacting compounds of the formula

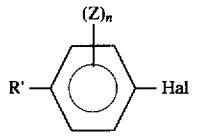

(15)

or compounds of the formula

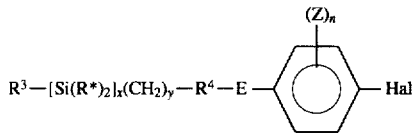

(36)

in which Hal is a halogen atom, preferably chlorine or bromine, with a meal, preferably magnesium, and reacting the resultant organometallic compound either with (b) compounds of the formula $$\text{Hal—COO—R''} \quad (16)$$

or $$\text{Hal—COO—R}^2 \quad (37)$$

in which Hal is as defined in the formula (15) and R" is as defined m the formula (8) and $R^2$ is as defined in the formula (30).

The abovementioned reactions (a) and (b) are preferably carried out in an aprotic, essentially anhydrous solvent. Examples of such solvents are the solvents mentioned above as being suitable for process 1.

Example 7 was carried out in accordance with process 3.

Process 4

Process 3 can also be modified by employing compounds of the formula (15) in which the radical R' has been replaced either by a radical of the formula $$H_2C{=}CH{-}(CH_2)_{y-2)}{-}R''''{-} \quad (18)$$

or a radical of the formula $$H{-}E{-} \quad (17)$$

or employing compounds of the formula (36) in which the radical of the formula $R^3{-}[Si(R^*)_2]_x(CH_2)_y{-}R^4{-}E{-}$ has been replaced by a radical of the formula $$H_2C{=}CH{-}(CH_2)_{y-2}{-}R^4{-}E{-} \quad (40)$$

or a radical of the formula $$H{-}R^4{-}E{-} \quad (41)$$

and the product obtained from the reaction is subsequently treated as in process 1 or process 2.

In the formula (17), E is preferably a divalent radical of the formula $-Si(CH_3)_2-$.

Use

The liquid-crystalline compounds according to the invention or the liquid-crystalline compounds which can be prepared according to the invention can be used in display devices, particularly in display devices produced using smectic liquid crystal (mixtures). In this case, it is possible to use pure compounds of the formula (8), mixtures thereof and in particular mixtures of liquid-crystalline compounds of the formula (8) with other liquid crystals. The compounds according to the invention are suitable for the preparation of smectic mixtures, in particular for mixtures which are capable of forming a smectic C phase. However, they may also be used as additives for nematic or cholesteric phases. The compounds of the formula (8) can be used both to prepare liquid-crystalline base mixtures and to positively modify the properties of ready-prepared base mixtures—such as, for example, the optical anisotropy, the electric anisotropy, the spontaneous polarization, the viscosity, the tilt angle, the pitch and the phase behavior.

The proportion of liquid-crystalline, silylated benzoic acid derivatives according to the invention in liquid-crystal mixtures may vary within broad limits depending on the intended use. It may be, for example, from 1 per cent by weight up to 100 per cent by weight.

If the compounds according to the invention are enantiomeric or diastereomeric, the present invention also includes the individual enantiomers or disstereomers and mixtures thereof, i.e. also racemates.

In the examples below, unless otherwise stated, a) all amounts relate to the weight:

b) all pressures are 0.10 MPa (abs.);

c) all temperatures are 20° C.

The phase descriptions are abbreviated as follows:

d) the numerical values denote transition temperatures, measured in °C.;

e) the phase types are characterized as follows:

i : isotropic phase, n : nematic phase, ch : cholesteric phase, sA : smectic A phase, sC : smectic C phase, sC*: chiral sine, tic C phase, sB : smectic B phase, s : smectic state of undetermined type, c : crystalline, G: glass state.

f) Phase descriptions in parentheses indicate super-coolable phases.

The nomenclature used in the examples below for the chemical compounds does not always correspond to the International Union of Pure and Applied Chemistry (IUPAC) rides. Thus, the radical called "pentamethyldisiloxyl" group in some examples is more correctly named the pentamethyldisiloxanyl group.

EXAMPLE 1

0.76 g (0.02 mmol of Pt) of 0.5% strength dicyclopentadienylplatinum dichloride solution (dichloromethane) was added to a solution of 18.0 g (36.1 mmol) of 4-octyloxyphenyl 4-(6'-hexenyloxy)benzoate in 20.0 g of dichloromethane, and 3.14 g (42.3 mmol) of trimethylsilane were passed in to the refluxing mixture over the course of 14 hours. After 8 hours, a further 0.76 g (0.02 mmol of Pt) of 0.5% strength dicyclopentadienylplatinum dichloride solution and after 12 hours a further 0.38 g (0.01 mmol of Pt) of 0.5% strength dicyclopentadienylplatinum dichloride solution were added. After complete hydrosilylation of the olefin, the reaction mixture was flushed with nitrogen, and the dichloromethane was removed by vacuum distillation on the rotary evaporator. The crude product was purified by chromatography on silica gel. The 4-octyloxyphenyl 4-(6'-trimethylsilylhexyloxy)benzoate obtained was additionally recrystallized from ethanol and exhibited the following phase behavior: c 47 sC 61 i.

The following were prepared analogously: 4- propyloxyphenyl 4-(3'-trimethylsilylpropyloxy)benzoate, phases: cl 65 c2 70 c3 85 i 4-butyloxyphenyl 4-(3'-trimethylsilylpropyloxy)benzoate, phases: c 73 (sA 44) i 4-octyloxyphenyl 4-(3'-trimethylsilylpropyloxy)benzoate, phases: c 54 (s 42 sC 49–50) i 4-octyloxyphenyl 4-(4'-trimethylsilylbutyloxy)benzoate, phases: c 49 (s 37 n 42) i 4-propyloxyphenyl 4-(5'-trimethylsilylpentyloxy)benzoate, phases: c 58–59 (sC 44–46) i 4-butyloxyphenyl 4-(5-trimethylsilylpentyloxy)benzoate, phases: c 63–64 (sC 56–57) i 4-octyloxyphenyl 4-(5-trimethylsilylpentyloxy)benzoate, phases: c 54 s 66 i 4-propyloxyphenyl 4-(6-trimethylsilylhexyloxy)benzoate, phases: c 66 (n 41) i 4-butyloxyphenyl 4-(6-trimethylsilylhexyloxy)benzoate, phases: c 61–62 (sC 48 n 52) i 4-(2'-(S)-methylbutyloxy)phenyl 4-(4-trimethylsilylbutyloxy)benzoate, phases: c 59 i 4-(2'-(S)-methylbutyloxy)phenyl 4-(5-trimethylsilylpentyloxy)benzoate, phases: c 68 (sC 32) i 4-(S)-2'-methylbutyloxyphenyl 4-(6-trimethylsilylhexyloxy)benzonte, phases: c 56 (sC 25–26) i 4-oxycarbonyl-(2'-(S)-chloroethyl)-phenyl-4-(6-trimethylsilylhexyloxy)benzoate phases: c 80 (sC 58–59) i 4,4'-pentylbiphenyl 4-(3-trimethylsilylpropyloxy)benzoate, phases: c 96 sC 113–115 sA 119–121 n 138 i 4,4'-pentylbiphenyl 4-(4-trimethylsilylbutyloxy)benzoate, phases: c 99 (s?/sC) s?/sC 109 n 142 i 4,4'-pentylbiphenyl 4-(4-trimethylsilylpentyloxy)benzoate, phases: c 100 sC 113 n 139 i 4-(4-trans-propylcyclohexylene)phenyl 4-(3-trimethylsilylpropyloxy)benzoate, phases: c 113–114 n 135 i 2-chloro4-octyloxyphenyl 4-(6-trimethylsilylhexyloxy)benzoate, phases: g —45 sC —16 n 12 i 4-octyloxyphenyl 3-chloro-4-(6-trimethylsilylhexyloxy) benzoate, phases: c 57 (sB 47) i

EXAMPLE 2

0.80 g (0.02 mmol of Pt) of 0.5% strength dicyclopentadienylplatinum dichloride solution (dichloromethane) was added to a solution of 15.0 g (39.0 mmol) of 4,4'cyanobiphenyl-4-(5-pentenyloxy)benzoate in 25.0 g of dichloromethane, and 4.00 g (53.9 mmol) of trimethylsilane were passed into the refluxing mixture over the course of 15 hours. After complete hydrosilylation of the olefin, the reaction mixture was flushed with nitrogen, and the dichloromethane was removed by vacuum distillation on a rotary evaporator. The crude product was purified by filtering through silica gel.

The product was subsequently recrystallized from diethyl ether and then chromatographed. The 4,4'-cyanobiphenyl 4-(5-trimethylsilylpentyloxy)benzoate obtained exhibited the following phase behavior: c 78 sA (psA) 219–222.

The following were prepared analogously:

4,4'-cyanobiphenyl 4-(6-trimethylsilylhexyloxy)benzoate, phases: c 90 sA 213 i 4,4'-cyanobiphenyl 4-(3-trimethylsilylpropyloxy)benzoate, phases: c 107–108 sA 200–204 i 4-cyanobiphenyl 4-(3 -trimethylsilylpropyloxy)benzoate, phases: c 82 (cl 52 (sA 27–28)) i 4-(5n-hexylpyrimidin-2-yl)phenyl 4-[5-(pentamethyldisiloxanyl)pentyloxy]benzoate, phases: c 83 (sI 35) sA 84 n 123 i 4-cyanophenyl 4-(4-trimethylsilylbutyloxy)benzoate, phases: c 68 i 4-cyanophenyl 4-(5-trimethylsilylpentyloxy)benzoate, phases: c 72–73 (sA 56–57) i 4-cyanophenyl 4-(6-trimethylsilylhexyloxy)benzoate, phases: c 72 (sA 59) i

EXAMPLE 3

0.94 g (0.024 mmol of Pt) of 0.5% strength dicyclopentadienylplatinum dichloride solution (dichloromethane) was added to a solution of 20.0 g (47.2 mmol) of 4-octyloxyphenyl 4-(5,-hexenyloxy)benzoate and 7.10 g (48.0 mmol) of pentamethyldisiloxane in 20.0 g of toluene, and the mixture was refluxed for 5 hours. After complete hydrosilylation of the olefin, the reaction mixture was flushed with nitrogen, and the toluene was removed by vacuum distillation on a rotary evaporator. The crude product was purified by chromatography on silica gel. The 4-octyloxyphenyl 4-(6-pentamethyldisiloxylhexyloxy)benzoate obtained was additionally recrystallized from ethanol and exhibited the following phase behavior: c 38 s :543 i.

The following were prepared analogously:

4-proploxyphenyl 4-(3-pentamethyldisiloxanylpropyloxy)benzoate, phases: c 50 i 4-octyloxyphenyl 4-(3-pentamethyldisiloxanylproploxy)benzoate, phases: c 30–33 i 4-octyloxyphenyl 4-(5-pentamethyldisiloxanylpentyloxy)benzoate, phases: sC 47 i 4-butyloxyphenyl 4-(6-pentamethyldiloxyanylhexyloxy)benzoate, phases: c 46(s 43–44) i 4-(2'-(S)-methylbutyloxy)phenyl 4-(3-pentamethyldisiloxanylpentyloxy)benzoate, phases: c 17 i 4-(2'-(S)-methylbutloxy)phenyl 4-(5-pentamethyldisiloxanylpentyloxyy)benzoate phases: c 62–63 i 4-(2'-(S)-methylbutyloxy)phenyl 4-(6-pentamethyldisiloxyanylhexyloxy)benzoate, phases: c 34 i 4-propylphenyl 4-(3-pentamethyldisiloxanlpropyloxy)benzoate, phases: c 36–37 (s) i 4-butylphenyl 4-(5-pentamethyldisiloxanylpentyloxy)benzoate, phases: c 7 (sC -2-1 sA 1–2) i 4,4'-pentylbiphenyl 4-(3-pentamethyldisloxanylpropyloxy)benzoate, phases: c 74–78 sA 106–107 i 4,4'-pentylbiphenyl 4-(4-pentamethyldisiloxylbutyloxy) benzoate, phases: c 80 sA 115–116 i 4,4'-pentylbiphenyl 4-(5-pentamethyldisiloxanylpentyloxy)benzoate, phases: c 79–81 sA 114–116 i 4,4'-pentylbiphenyl 4-(6-pentamethyldisiloxylhexyloxy) benzoate, phases: g 56 sA 128–131 i 4,4'-ethylbiphenyl 4-(3-pentamethyldisiloxanylproploxy)benzoate, phases: c 77 sC 92 sA 92–93 i 4-(4-trans-propylcyclohexylene)phenyl 4-(3-pentamethyldisiloxanylproploxy)benzoate, phases: c 105 i 2-chloro-4octyloxyphenyl 4-(6-pentamethyldisiloxanyl-hexyloxy)benzoate, phases: g —54 s —2 i

EXAMPLE 4

0.94 g (0.024 mmol of Pt) of 0.5% strength dicyclopentadienylplatinum dichloride solution (dichloromethane) was added to a solution of 13.8 g (42.9 mmol) of 4-cyanophenyl 4-(5-hexenyloxy)benzoate and 6.48 g (43.7 mmol) of pentamethyldisiloxane in 50.0 g of toluene, and the mixture was refluxed for 3 hours. After complete hydrosilylation of the olefin, a further 0.94 g (0.024 mmol of Pt) of 0.5% strength dicyclopentadienylplatinum dichloride solution (dichloromethane) were added, and the mixture was refluxed for a further 2 hours. The reaction mixture was flushed with nitrogen, and the toluene was removed by vacuum distillation on a rotary evaporator. The crude product was purified by chromatography on silica gel. The 4-cyanophenyl 4-(6-pentamethyldisiloxanylhexyloxy)benzoate obtained was additionally recrystallized from petroleum ether (100° C.–140° C.) and exhibited the following phase behavior: c 54–55 (sA 53–55) i.

The following were prepared analogously:

4-cyanophenyl 4-(3-pentamethyldisiloxanylpropyloxy)benzoate, phases: c 65 (sA 26–28) i 4-cyanophenyl 4-(4-pentamethyldisiloxanylbutyloxy)benzoate, phases: c 68 i 4-cyanophenyl 4-(5-pentamethyldisiloxanylpentyloxy)benzoate, phases: sA 55–56 i 4,4'-cyanibiphenyl-4-(3-pentamethyldisiloxanlpropyloxy)benzote, phases: c 86 sA 209–210 i (4,4'-cyanobiphenyl-4-(5-pentamethyldisiloxanylpentyloxy)benzoate, phases: c 48 sA 215 i 4,4'-cyanobiphenyl 4-(6-heptamethyltrisiloxanylhexyloxy)benzoate, phases: c+sA 39 sA 193–197 i 4,4'-cyanobiphenyl 4-(6-nonamethltetrasiloxanylhexyloxy)benzoate, phases: sC 91 sA 178–181 i 4,4'-cyanobiphenyl 4-(6-undecamethylpentasiloxanylhexloxy)benzoate, phases: sC 77 sA 154–156 i 4,4'-cyanobiphenyl 4-(6-tridecamethylhexasiloxanylhexyloxy)benzoate, phases: sC 43 sA 135–141 i 4,4'-cyanobiphenyl 4-(6-pentadecamethylheptasiloxanylhexyloxy)benzoate, phases: sC 42 sA 127–129 i.

EXAMPLE 5

0.18 g (4.6 μmol of Pt) of 0.5% strength dicyclopentadienylplatinum dichloride solution (dichloromethane) was added to a refluxing solution of 2.00 g (11.0 mmol) of 4-but-3-enyloxychlorophenol and 6.00 g (10.9 mmol) of cholesteryl 4-dimethylsilylbenzoate m 10.0 g of toluene, and the mixture was refluxed for 1 hour. After complete hydrosilylation, the toluene was removed by vacuum distillation on a rotary evaporator, The crude product was purified by chromatography on silica gel. The cholesteryl 4-(4'-chlorophenyloxybutyldimethylsilyl)benzoate obtained was additionally reprecipitated from toluene using methanol and exhibited the following phase behavior: c 88–94 (G 12 ch 54) i.

The following were prepared analogously:

cholesteryl 4-(4'-chlorophenyloxypropyldimethylsilyl)benzoate, phases: c 88 (G 13 s 69) i cholesteryl 4-(4'-biphenyloxypropyldimethlsilyl)benzoate, phases: G 28 s 128–132 i cholesteryl 4-(4'-cyanophenyloxypropldimethylsilyl)benzoate, phases: G 21 n 51 i cholesteryl 4-(4'-cyanophenyloxybutyldimethylsilyl)benzoate, phases: c 84 (G15 ch 68) i cholesteryl 4-(4'-cyanophenyloxypentyldimethylsilyl)benzoate, phases: c 66 (G 10) i cholesteryl 4-(4'-methoxyphenyloxypropyldimethylsilyl)benzoate, phases: c 50-60 (G 10) i cholesteryl 4-(4'-chlorophenloxycarbonylphenyl-4"-oxypropldimethylsilyl)benzoate, phases: c 146–151 (s) i cholesteryl 4-(4'-cyanophenyloxycarbonylphenyl-4"-oxypropyldimethylsilyl)benzoate, phases: c 128–137 (s) i cholesteryl 4-(4'-cyanophenyloxycarbonlphenyl-4"-oxybutyldimethylsilyl)benzoate, phases: G 31 ch 157 i cholesteryl 4-(4'-cyanophenyloxycarbonylphenyl-4"-oxypentyldimethylsilyl)benzoate, phases: c 104 (G 27) i cholesteryl 4-(cholesteryloxycarbonylphenyl-4'-oxypropyldimethylsilyl)benzoate, phases: c 189 (s 132 ch 179) i cholesteryl 4-(cholesteryloxycarbonylphenyl-4'-oxy)butyldimethylsilyl)benzoate, phases: c 199 ch 231–234 i cholesteryl 4-(cholesteryloxycarbonylphenyl-4'-oxypentyldimethylsilyl)benzoate, phases: c 186–195 (G43 s 148 ch 182) i cholesteryl 4-(cholesteryloxycarbonylphenyl-4'-oxypentyldimethylsilyl)benzoate, phases: c 173 sA 202 ch 218 i cholesteryl 4-(4'-methoxyphenyloxycarbonylphenyl-4"-oxypropyldimethylsilyl)benzoate, phases: c 90 s 112–114 i cholesteryl 4-(4'-methoxyphenyloxycarbonylphenyl-4"-oxybutyldimethylsilyl)benzoate, phases: c 153 (G 21 ch 143) i cholesteryl 4-(4'-methoxyphenyloxycarbonylphenyl-4"-oxypentyldimethylsilyl)benzoate, phases G 24 s 62–74 i cholesteryl 4-(4'-biphenyloxycarbonylphenyl-4"-oxypropyldimethylsilyl)benzoate, phases: c 144 (G 36 s 90–97) i 4'-biphenyl 4-(cholesteryloxycarbonylphenylene-4'-oxypropyldimethylsilyl)benzoate, phases: c 131 (G 32 s 106) i 4'-biphenyl 4-(cholesteryloxycarbonylphenylene-4'-oxybutyldimethylsilyl)benzoate, phases: c 126 (G 40 s? 56) ch 189 i 4-biphenyl 4-(cholesteryloxycarbonylphenyl-4'-oxypentyldimethylsilyl)benzoate, phases: c 112 (G 25 s 50–73)ch 109 i (135 i)

4'-biphenyl 4-(cholesteryloxycarbonylphenylene-4"-oxyhexyldimethylsilyl)benzoate, phases: G18 ch 152 i 4-biphenyl 4-(4'-methoxyphenyloxycarbonylphenyl-4"-oxypropyldimethylsily)benzoate,recrystallization:-toluene, phases: c 134–144 i 4-biphenyl 4-(4'-methoxyphenloxycarbonlphenyl-4"-oxybutyldimethylsilyl)benzoate, phases: c 147–152 (s 50–70 n 100–110) i 4-biphenyl 4-(4'methoxyphenyleneoxycarbonylphenylene-4"-oxypentyldimethylsilyl)benzoate, phases: c 121 i 4-chlorophenyl 4-(cholesteryloxycarbonylphenylene-4'-oxypropyldimenthylsilyl)benzoate, phases: c 141–143 (s 141–146) i 4-chlorophenyl 4-(4'-methoxyphenyloxycarbonylphenylene-4"-oxypropyldimethylsilyl)benzoate, phases: c 105 i 4-cyanophenyl 4-(cholesteryloxycarbonylphenylene-4'-oxypropyldimethylsilyl)benzoate, phases: c 154–158 (G 40 ch 119) i 4-cyanophenyl 4-(4'-biphenyloxycarbonylphenylene-4"-oxypropyldimethylsilyl)benzoate. phases: G 28 s 129 i 4-cyanophenyl 4-(4'-methoxyphenloxycarbonyphenyl-4"-oxypropyldimethylsilyl)benzoate, phases: c 142–146 i 4-methoxyphenyl 4-(cholesteryloxycarbonylphenylene-4'-oxypropyldimethylsilyl)benzoate, phases: c 137 i 4-methoxyphenyl 4-(4'-biphenyloxycarbonlphenylene-4"-oxypropyldimethylsilyl)benzoate, phases: c 118 i 4-methoxyphenyl 4-(4'-methoxyphenyloxycarbonyl-phenylene-4"-oxypropyldimethylsilyl-)benzoate, phases: c 128–135 i 2'-(S)-methylbutyl 4-(cholesteryloxycarbonylphenylene-4'-oxypropyldimethylsilyl)benzoate, phases: c 83 (G—25 s 17 sC 71) i 4-phenylencarbonyloxy-2'-(S)-methylbutyl 4-(cholesteryloxycarbonylphenylene-4'-oxypropyldimethylsilyl)benzoate, phases: c 101 (G 23 s 43–48) i phenylene-4-carbonyloxy-2'-(S)-methylbutyl 4-(4'-methoxyphenyloxycarbonylphenylene-4"-oxypropyldimethylsilyl)benzoate, phases: c 67 i 4-hydroxycyclohexyl 4-(4'-methoxyphenyloxycarbonylphenylene-4"-oxypropyldimethylsilyl)benzoate, phases: G 18 s 132 i 4,4'-methoxybiphenyl 4-(cholesteryloxycarbonylphenylene-4'-oxypropyldimethylsilyl)benzoate, phases: c 157–160 ch 179 i 4,4'-cyanobiphenyl 4-(cholesteryloxycarbonylphenylene-4'-oxypropldimethylsilyl)benzoate, phases: c 165 (G 39 sC 148) ch 202–213 i 4,4'-cyanobiphenyl 4-(cholesteryloxycarbonylphenylene-4'-oxybutyldimethylsilyl)benzoate, phases: c 160 (G 37) sC 190 ch 238 i 4,4'-cyanobiphenyl 4-(cholesteryloxycarbonylphenylene-4'-oxypentyldimethylsilyl)benzoate, phases: c 115 (G 32 s 139) sA 185–186 ch 216 i 4,4'-cyanobiphenyl 4-(cholesteryloxycarbonylphylene-4'-oxyhexyldimethylsilyl)benzoate, phases: c 143 (G 28) sA 227–228 ch 243 i 4,4'-methoxybiphenyl 4-(4'-methoxyphenyleneoxycarbonylphenylene-4"-oxypropyldimethylsilyl)benzoate, phases: c 133–135 (S 95) i

EXAMPLE 6

The following were prepared by known methods:

4-cyanophenyl 4-[6-trimethylsilyl)hexyl]benzoate m.p.: 43° C., on cooling, a smectic phase forms from 39.7° C. which recrystallizes at 33.5° C.

4-(4-methoxyphenyl)ethylphenyl 4-(6-trimethylsilylhexyl-1)benzoate, c 64 n 84 i 4-butylphenyl 4-[4-(trimethylsilyl)butyl]benzoate, c 21 i 4-propylphenyl 4-[5-trimethylsilyl)pentyl]benzoate, liquid, (G)—60 i 4-propylphenyl 4-[3-(pentamethyldisiloxanyl)propyl]benzoate, (G)—69 i 4-butylphenyl 4-[4-(pentamethyldisiloxanyl)butyl]benzoate, (G)—19 i 4-butylphenyl 4-[5-pentamethyldisiloxanyl)pentyl]benzoate, c —32 i 4-butylphenyl 4-[6-(pentamethyldisiloxanyl)hexyl]benzoate, c —28 i 4-butoxypheny 4-[3-pentamethyldisiloxanyl)propyl]benzoate, c 40 i 4-cyanophenyl 4-[3-(pentamethyldisiloxanyl)propyl]benzoate, c 19 i 4-cyanophenyl 4-[5-(pentamethyldisiloxanyl)pentyl]benzoate, c 27 i 4-cyanobiphenylyl 4-[3-(pentamethyldisiloxanyl)propyl] benzoate, c 121 n 165 i 4-cyanobiphenylyl 4-[12 -(trimethylsilyl)dodecyl]benzoate, c 64–66 sA 191 i 4-cyanobiphenyl 4-[12-(pentamethyldisiloxanyl)dodecyl] benzoate, c 35 c, sA 46 sA 183 i 4-n-octyloxyphenyl 4-[5-(pentamethyldisiloxanyl)pentyl] benzoate, c 37 i 4-butylphenyl 4-[10-(trimethylsilyl)decyl]benzoate, metastable n, c 12–21 i 4-cyanobiphenyl 4-[6-(dimethylethylsilyl)hexyl]benzoate, c 66 sA 187–190 i 4-cyanobiphenylyl 4-[7-(trimethylsilyl)heptyl]benzoate, c 64 sA 189i 4-n-octyloxyphenyl 4-[5-(trimethylsilyl)pentyl]benzoate, c 29–31 i 4-n-octylphenyl 4-[4-(butyldimethylsilyl)butyl]benzoate, c —2 i 4-cyanobiphenylyl 4-[5-(heptamethyltrisloxanyl)pentyl] benzoate, GF, C 3F sA 159–160;, 4-n-octyloxyphenyl 4-[4-(pentamethyldisiloxanl)butyl(4-phenyl)ethyl]benzoate, sG 36–41 sC 83–86 i 4-cyanobiphenylyl 4-[4-(pentamethyldisiloxanyl)butyl-(4-phenyl)ethyl]benzoate, c 68–70 sA 230–232 i 4'-(5-hexylpyrimidin-2-yl)phenyl 4-(5-trimethylsilylpentyloxy)benzoate, c 83 (sI 35) sA 84 n 123 i.

EXAMPLE 7

12.3 g (0.1 mol) of commercially available chloromethyltrimethylsilane were dissolved in 100 ml of diethyl ether, and this solution was added dropwise over the course of one hour with stirring at 20° C. and under a protective gas to a mixture of 3 g of magnesium turnings, an initiating amount of 2 ml of the above mixture and a trace of ethyl iodide after the reaction had commenced. When the addition was complete, the mixture was refluxed for a further 30 minutes, then cooled and decanted from the excess magnesium. The solution obtained was added dropwise over the course of 30 minutes with stirring at 20°–30° C. to a solution of 22.7 g (0.1 mol) of 2-(4-chlorophenyl)ethyl toluenesulfonate (obtainable from commercially available 2-(4-chlorophenyl)ethanol by customary reaction with toluenesulfonyl chloride) in 100 ml of tetrahydrofuran. When the addition was complete, 100 ml of the solvent mixture were moved by distillation and replaced by 50 ml of tetrahydrofuran. The mixture was heated at an internal temperature of 60° C. for 60 minutes, during which a precipitate of magnesium tosylate formed. After cooling, the mixture was poured onto ice and acidified using a little hydrochloric acid, and the aqueous phase was extracted twice with tert.butyl methyl ether. The combined organic phases were washed with NaCl solution, dried and evaporated. Fractional distillation of the residue at 16 hPa and 115°–118° C. gave 17.1 g (75.4% of theory) of 1-(1-trimethylsilylpropyl)-4-chlorobenzene.

2 g of magnesium were introduced into a flask, and 7 ml of a 1:1 mixture of the silane mentioned and tetrahydrofuran were added at 40° C. in order to initiate the reaction. After an internal temperature of 75° C. had been reached, the remainder of the silane/THF mixture (corresponding to 14 g of the silane) was added dropwise over the course of 30 minutes without external heating. The mixture was subsequently refluxed for 1 hour, then cooled and separated from the excess magnesium by filtration.

This solution was added dropwise at room temperature to a mixture of 13 g (0.07 mol) of commercially available 4-methoxyphenyl chloroformate and 40 ml of tetrahydrofuran. The exothermic reaction was kept at 15° C. by external cooling. When the addition was completed, the mixture was refluxed for 2 hours, during which time a precipitate formed. After cooling, the mixture was poured onto ice and acidified using 2N sulfuric acid, and the phases were separated. The aqueous phase was extracted twice with tert.butyl methyl ether, and the organic phases were washed with NaCl solution, dried and evaporated. Chromatography of the residue on silica gel using a 50:1 mixture of petroleum ether (boiling point 50°–75° C.)/ethyl acetate as eluent gave 5.6 g of liquid 4-methoxyphenyl 4-(1-trimethylsilylpropyl)benzoate. $^1$H NMR spectrum ($CDCl_3$ as the solvent) of the ester:

0.1 ppm (s, $SiMe_3$); 0.5–0.7 ppm (m, $Me_3Si$-$\underline{CH_2}$); 1.6–1.8 ppm (m, $Me_3SiCH_2$—$\underline{CH}$); 3.8 ppm (t, J=6.0 Hz, $C_6H_4$—$\underline{CH_2}$); 3.9 ppm (s, $OCH_3$); 6.9–7.2 ppm (m, 4 aromatic H of the benzoic acid); 7.2–8.2 ppm (m, 4 aromatic H of the phenol moiety) in the ratio 9:2:2:2:3:4:4.

EXAMPLE 8

0.35 g (0.01 mmol of Pt)of0.5% strength dicyclopentadienylplatinum dichloride solution in dichloromethane was added as catalyst to a solution of 5.00 g (9.71 mmol) of 4-(5-hexenyloxy)phenyl 4-(3-butenyloxy)benzoate in 10 ml of dichloromethane, and 2.02 g (27.2 mmol) of trimethylsilane were passed into the refluxing mixture over the course of 8 hours. After complete hydrosilylation of the olefin, the reaction mixture was flushed with nitrogen, and the dichloromethane was removed by vacuum distillation on a rotary evaporator. The crude product was purified by chromatography on silica gel, to give 4-(1-trimethylsilylhexyloxy)phenyl 4-(1-trimethylsillbutyloxy)benzoate, phases: c 72 i.

EXAMPLE 9

0.48 g (0.012 mmol of Pt) of 0.5% strength dicyclopentadienylplatinum dichloride solution in dichloromethane was added as catalyst to a solution of 5.00 g (7.54 mmol) of 4-(5-hexenyloxy)phenyl 4-(3-butenyloxy)-benzoate and 4.05 g (27.3 mmol) of pentamethyldisiloxane in 15.0 g of toluene, and the mixture was refluxed for 4 hours. After complete hydrosilylation, the toluene was removed by vacuum distillation on a rotary evaporator. The crude product was purified by chromatography on silica gel, to give 4-(1-pentamethyldisiloxylhexyloxy)phenyl 4-(1-pentamethyldisiloxylbutyloxy)benzoate, phases: c 15 (s) i.

The following were prepared analogously: 4,4'-(bis-4-(1-pentamethyldisiloxylpropyloxy)benzoyloxy)biphenyl, phases: cl 79 c2 195 i 4-(1-pentamethyldisiloxylhexyloxy)phenyl 4(1-pentamethyldisiloxylpropyl)benzoate, phases: c 10 (s<–15) i.

EXAMPLE 10

20.0 g (0.101 mol) of 4-dimethylsilylbenzoyl chloride were added dropwise at 10 C–15 C to a solution of 8.90 g (0.101 mol) of 2-methylbutan-1-ol in 20 ml of dry pyridine. The reaction solution was stirred for one hour at 25° C., poured onto ice and acidified using HCl. The organic phase was separated off, diluted with toluene and washed by shaking three times with 10% HCl. It was washed with water and dried over sodium sulfate. After the toluene had been stripped off in vacuo on a rotary evaporator, distillation gave 2-methylbutyl 4-methylsilylbenzoate; boiling point 86 C–110 C/0.05 mmHg.

The following were prepared analogously:

4-(4'-cyano)biphenyl 4-dimethylsilylbenzoate; recrystallized from cyclohexane/toluene)(4:1), [c 142 n 167 i];

4-(4'-methoxy)biphenyl 4-dimethylsilylbenzoate; recrystallized from cyclohexane, [c 141 n 148].

Use examples for novel intermediates of the formula (53)

EXAMPLE 11

Surface treatment of glasses

The glasses used were degreased in an ultrasound bath containing ethanol and subsequently dried. A 2% strength solution (% by weight) of 4,4'-cyanobiphenyl 4-dimethylsilylbenzoate containing 2.5 mol% of Pt in the form of dicyclopentadienylplatinum dichloride was dripped onto these glasses and dried at 100 C for 30 minutes. The treated glasses were washed with toluene and acetone and re-dried. A 10 μ thick layer phase 5 from Merck, applied to glasses treated in this way, was oriented perpendicular to the glass plates.

The following were used analogously: 4,4'-methoxybiphenyl 4-dimethylsilylbenzoate; 4-biphenyl 4-dimethylsilylbenzoate; cholesteryl 4-dimethylsilylbenzoate; 4-(w-alkenyl)benzoic acid esters which can be employed in process 1, and the phase descriptions thereof 4-propylphenyl 4-allylbenzoate, c 29 i; 4-butylphenyl 4-allylbenzoate, c 30 i; 4-propoxyphenyl 4-allylbenzoate, c 60 i; 4-butoxyphenyl 4-allylbenzoate, c 57 i; 4-octyloxyphenyl 4-allylbenzoate, c 42 i; 4-cyanophenyl 4-allylbenzoate, k 108 i: 4-cyanobiphenylyl 4-allylbenzoate, c 113–118 c, n 125 n 239–246 i; 4-propylphenyl 4-(3-butenyl)benzoate, c 24 i; 4-butylphenyl 4-(3-butenyl)benzoate, c 13 i; 4-methoxyphenyl 4-(3-butenyl)benzoate, c 54 89 i; 4-propoxyphenyl 4-(3-butenyl)benzoate, c 54–59 i; 4-butoxyphenyl 4-(3-butenyl)benzoate, c 58 n 59 i; 4-octyloxyphenyl 4-(3-butenyl)benzoate, c 42 n 67 i; 4-cyanophenyl 4-(3-butenyl)benzoate, c,n 75 c,i 177 i; 4-cyanobiphenylyl 4-(3-butenyl)benzoate, c 95–124 n 260 i; 4-chlorophenyl 4-(3-butenyl)benzoate, c 53 i; 4-biphenylyl 4-(3-butenyl)benzoate, c 93 n 105 i; 4-propylphenyl 4-(4-pentenyl)benzoate, b.p. (0.06 hPa) 176 C; 4-butlphenyl 4-(4-pentenyl)benzoate, c —4 i; 4-cyanophenyl 4(4-pentenyl)benzoate, c 40 i; 4-cyanobiphenylyl 4-(4-pentenyl)benzoate, c 42 n 63 i; 4-propylphenyl 4-(5-hexenyl)benzoate c 2 i; 4-butylphenyl 4-(5-hexenyl)benzoate, c 9 i; 4-octyloxyphenyl 4-(5-hexenyl)benzoate, c 40 n 57 i; 4-cyanophenyl 4-(5-hexenyl)benzoate, c 63 i; 4-cyanobiphenylyl 4-(5-hexenyl)benzoate, c 132 n 239 i.

What is claimed is:

1. A liquid crystalline compound of the formula

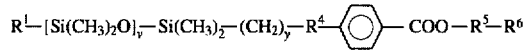

(62)

in which $R^1$ is a $C_1$- to $C_{18}$ alkyl group, v is an integer having a value of from [0] *1* to 10, y is an integer of from 3 to 12, $R^4$ is selected from the group consisting of a single chemical bond, a radical of the formula

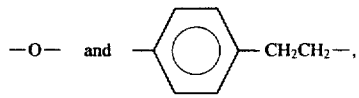

(45)

$R^5$ is a radical selected from the group consisting of divalent radicals of the formulas and halogenated, divalent radicals of the formulas

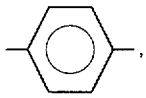

(42)

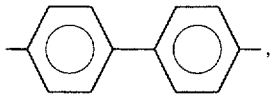

(43)

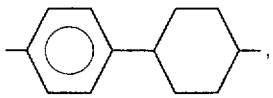

(44)

-continued (60)

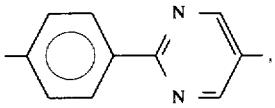

(63)

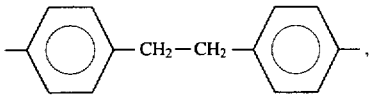

(64)

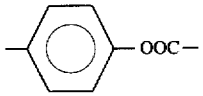

and

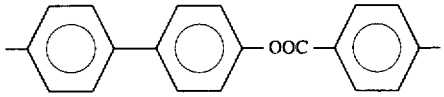

and $R^6$ is selected from the group consisting of $R^1$, a halogen atom, a cyano group, a hydrogen atom, a $C_1$- to $C_{18}$ alkoxy group, a $C_1$- to $C_{18}$ alkyl group substituted with chlorine atoms and a group of the formula $$-O-(CH_2)_y-Si(CH_3)_2-[OSi(CH_3)_2]_v-R^1, \qquad (66)$$

where y, v and $R^1$ are the same as above, with the proviso that if $R^5$ is a group of formula 64, $R^6$ is a $C_1$–$C_{18}$ alkyl group substituted with chlorine atoms.

[2. A compound of claim 1, wherein the compound is 4-octyloxyphenyl-4-(6-trimethylsilylhexyloxy)benzoate.]

3. A display device containing the liquid crystalline compound of claim 1.

* * * * *